United States Patent [19]

Tauber et al.

[11] 4,282,016

[45] Aug. 4, 1981

[54] GAS AND FAILURE PARTICLE SEPARATOR SYSTEM

[75] Inventors: Thomas E. Tauber, Lansdowne; George E. Chapman, Woodlyn, both of Pa.

[73] Assignee: Technical Development Co., Glenolden, Pa.

[21] Appl. No.: 126,102

[22] Filed: Feb. 29, 1980

Related U.S. Application Data

[63] Continuation-in-part of Ser. No. 8,526, Feb. 1, 1979, abandoned.

[51] Int. Cl.³ .................... B01D 35/14; B01D 45/16; B01D 19/00
[52] U.S. Cl. .................................. 55/204; 55/459 R; 210/85; 210/223; 210/304; 210/512.1
[58] Field of Search ............ 55/204, 205, 178, 459 R; 134/10; 209/211, 144; 210/85, 93, 223, 304, 425, 512 R, 86, 222, 311; 324/204

[56] References Cited

U.S. PATENT DOCUMENTS

| | | | |
|---|---|---|---|
| 2,010,435 | 8/1935 | Matheson | 210/512 R X |
| 2,016,642 | 10/1935 | Lincoln | 210/512 R X |
| 2,375,826 | 5/1945 | Scott | 209/211 |
| 2,936,890 | 5/1960 | Botstiber | 210/86 |
| 2,952,330 | 9/1960 | Winslow | 55/204 X |
| 3,127,255 | 3/1964 | Winslow | 55/204 X |
| 3,317,042 | 5/1967 | Botstiber | 210/86 |
| 3,432,750 | 3/1969 | Botstiber | 324/204 |
| 3,726,068 | 4/1973 | Lowrie | 210/512 R X |
| 4,008,464 | 2/1977 | Hobbie | 210/85 X |
| 4,199,443 | 4/1980 | Tauber | 210/512.1 X |

FOREIGN PATENT DOCUMENTS 994351 6/1965 United Kingdom .................... 209/211

Primary Examiner—Robert H. Spitzer
Attorney, Agent, or Firm—Robert S. Lipton

[57] ABSTRACT

An apparatus for removing entrapped gas and selectively removing and detecting particles above a predetermined size in an oil lubrication system is described. The oil enters tangentially at the top of an outer cylinder and is caused to cyclonically work its way down to the bottom of the cylinder. The oil is then forced to reverse its flow and travel up along an inner cylinder. The centrifugal force fields created by such flow cause entrapped gas to coalesce in the center of the flow pattern from which point it can be vented from the system. It also causes heavier particles, which are used by the apparatus to detect impending failure, to be thrown out of the flow pattern into a detection cavity positioned at the bottom of the outer cylinder at its periphery while lighter particles remain suspended in the fluid. A conventional magnetic sensor is contained within the cavity to capture the separated particles for subsequent removal from the system and signal their presence to the operator of the system.

4 Claims, 3 Drawing Figures

GAS AND FAILURE PARTICLE SEPARATOR SYSTEM

BACKGROUND OF THE INVENTION

This is a continuation-in-part application of U.S. patent application Ser. No. 8,526, filed Feb. 1, 1979 and entitled "Gas and Failure Particle Separator System", now abandoned.

This invention relates generally to combination particle detectors and foam separators which are used in conjunction with hydraulic and lubrication systems for mechanical equipment which utilize a fluid such as oil. In particular, the invention selectively removes particles above a predetermined size in the oil of such systems. The invention is further adapted to remove air and other trapped gases from the fluid and vent them from the system.

Mechanical power transmission equipment is subject to wear due to abrasion, caused by the contact of moving parts under pressure at high relative speeds. This results in the release of a quantity of small particles. Such "wear particles" or "fuzz" are generally 2 to 20 microns in size. Particles of this size, when suspended in a circulating fluid such as heavy lubricating oil generally move with it rather than reacting promptly to gravity and inertial forces. However, once normal "wear in" occurs the quantity of such particles reduces to a relatively low value which in most systems are readily removed from the system through the use of suitable filters or by strategically placed magnets, if the particles are of a ferrous nature. When the components of the power transmitting system which is being lubricated become overloaded or when localized areas of weakness occur, the situation changes radically. In such cases much larger particles of material become loosened, generally at the point of contact between moving parts under high surface pressure. Furthermore once the surface has been deformed by the breaking off of such particles the rate of deterioration accelerates resulting in the breaking off of additional particles at increasing rates. Additionally, the quantities of wear particles produced are substantially increased. Failure particles generally fall into the 100 to 2000 micron size range. Due to their greater mass they are less subject to being suspended in the lubricating fluid.

It is well known that the structural failure of drive train components may be predicted in advance of such failure by monitoring the condition of the lubricating oil. Such structural failure is indicated when metallic particles in the size range of failure particles, i.e. greater than 100 microns, are detected or when the quantity of wear particles substantially increases. The present invention is of the type that separates out such failure particles and provides a signal warning the operator of the situation occurring.

The prior art is replete with descriptions of various apparatus which will detect the presence of failure particles. Some of these apparatus use filters of varying mesh size which are periodically checked so as to determine the presence of failure particles. This approach is not appropriate for aircraft applications as it does not lend itself to inflight monitoring. Other apparatus use electronic devices wherein failure particles are detected by the disturbance of a magnetic or electric field by such particles. A problem associated with such apparatus has been that a collection of wear particles is detected as a failure particle thus resulting in a false indication. Additionally, such magentic detectors are highly dependent upon the sensor which is used in determining the overall accuracy and sufficiency of the apparatus. U.S. Pat. No. 2,936,890 issued May 17, 1960 and U.S. Pat. No. 3,432,750 issued Mar. 11, 1969 to Botstiber are examples of magnetic chip detectors. U.S. Pat. No. 3,317,042 issued May 2, 1967 to Botstiber is an example of an apparatus which combines a filter with a circuit completion type sensor.

In addition to generating particulate debris, power applications also tend to create a degree of churning of the lubricating fluid with resultant formation of foams which are often highly stable. In many systems equal amounts of air, by volume, are mixed with oil. In still other high speed applications such as in the lubrication systems for gas turbines as many as four parts of air may be mixed with one part of oil, by volume. Such dilution of the oil is obviously undesirable since it results in less oil coming in contact with the surfaces requiring lubrication thus diminishing the lubricating effect of the oil. The presence of air in the oil results in the air being compressed thus lowering the overall oil system pressure, this is particularly true when displacement type pumps are used as is common in these types of systems. Additionally, the cooling effect of the oil is substantially reduced. This, of course, increases the probabilities of over heating and accelerated wear. Various means are disclosed by the prior art for removing air from a lubricating fluid. However, none of these "foam breakers" are combined with a device designed to remove debris particles at the same time. As a result separate devices must be used which, of necessity, increases both the weight and complexity of such systems. This is particularly undesirable and detrimental for aircraft application.

SUMMARY OF THE INVENTION

The present invention mechanically segregates failure particles from wear particles thus increasing the reliability and accuracy of the detection of the failure particles by conventional detection equipment. The invention is further adapted so as to include means for removing air and other entrapped gases from the fluid.

The invention includes two inner hollow cylindrical tubes which are encompassed by and connected to an outer cylindrical housing. The first of these tubes enters from the top of the housing and extends only part way toward the bottom of the housing. This serves as the air outlet. The second inner tube enters from the bottom of the housing and is the oil outlet. The lubricating fluid enters tangentially the top of the housing and cyclonically works its way around both of the inner tubes to the bottom of the housing in a spiral flow pattern where it then rises to and enters the top of the second tube from which it exits the housing. The top of this tube is shrouded to prevent any substantial loss of oil into gas outlet.

The housing further contains a detection cavity formed at its bottom at or near its periphery for receiving failure particles. While normal wear particles, which are suspended in the fluid travel along with it, the heavier failure particles are forced against the inner surface of the housing by centrifugal force and then down to the bottom of the housing where they are thrust into the detection cavity. Conventional magnetic particle detection equipment is contained within this cavity which is also adapted to indicate the presence of the subject failure particles.

The cyclonic motion of the oil also serves to separate out the gases. This happens because the foam has a lower specific gravity than the oil, and is therefore, subject to substantially lower centrifugal force. Consequently the gas forms a column in the center of the housing as the oil rotates around the upper inner cylinder and is captured by the gas collector. The gas may be vented through the use of an external pressure valve thereby permitting the lubrication system pressure to be maintained.

Accordingly, it is the object of the present invention to provide an apparatus which will separate failure particles from wear particles and which will separate entrapped gases in the fluid of a lubricating system for mechanical drive systems.

It is another object of the present invention to provide means for separating failure particles from wear particles and entrapped gases in the fluid of lubrication systems, wherein centrifugal force is used to provide such separation.

Other and further objects and advantages of the invention will become apparent from a consideration of the drawings and the discussion which follows.

DESCRIPTION OF THE PREFERRED EMBODIMENT

Figure 1:
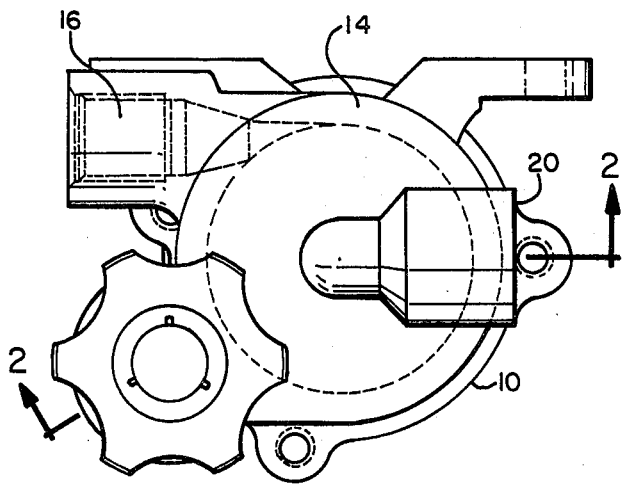
FIG. 1 is a top view of a particle and gas separator according to the present invention.
Figure 3:
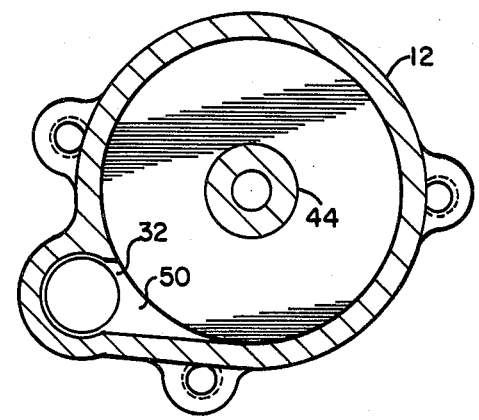
FIG. 3 is a horizontal cross section along line 3—3 in FIG. 2.
Figure 2:
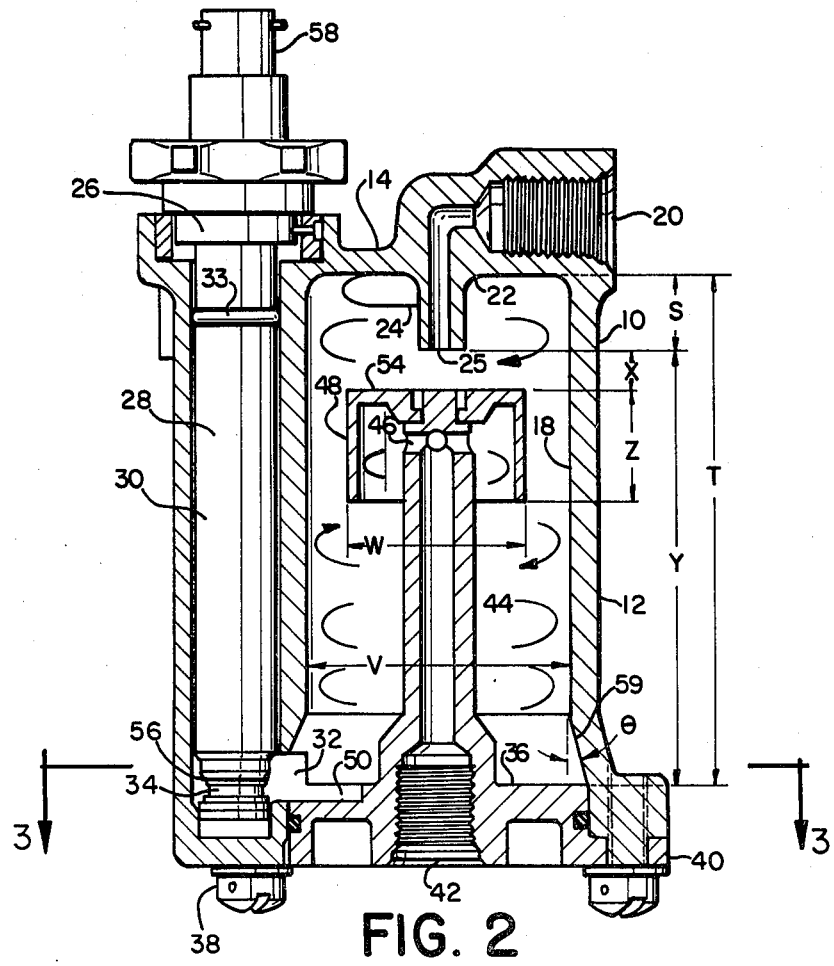
FIG. 2 is a vertical cross section side view along line 2—2 in FIG. 1.

Referring now to FIGS. 1, 2, and 3 we see several views illustrating the preferred embodiment of a combination particle and gas separation system 10 according to the present invention. In the preferred embodiment it comprises a hollow cylindrical housing 12 having an integral top 14. Built into said top is oil inlet 16, which receives the fluid from the oil hydraulic system (not shown) and is adapted to inject said fluid tangentially to the smooth inner wall 18 of said hollow housing.

Top 14 further contains a gas outlet or discharge 20 which is connected through internal channel 22 to a short hollow cylindrical tube 24, which, in turn, is concentric with housing 12. Tube 24 also cooperates with inner wall 18 to form a cylindrical annulus, which as will be explained below, is critical to the total operation of the system herein described. Tube 24 has but a single opening 25 at its tip which acts as an inlet for the separated gas and foam for subsequent discharge from the system.

Also contained in top 24 is an opening 26 leading into chamber 28, which lies alongside the full length of hollow housing 12 and is further adapted to contain a magnetic particle detector 30. At the bottom of chamber 28 is an exit hole 32, through which separated particles are attracted by magnet 34 of detector 30. As shown in FIG. 2 maximum particle capture efficiency is achieved by having said magnet positioned at the same reference point along the length of housing 12 as is hole 32. Oil pressure is maintained in chamber 28 by an "O" ring 33 or similar type of sealing device.

Housing 12 is closed at the bottom with plate 36 which in the preferred embodiment is held in place with a plurality of bolts 38 which screw into lugs 40 in housing 12. Built into said plate is fluid outlet 42 to which a second hollow tube 44 is attached and which, like tube 24 is concentric with housing 12 extending up into the hollow interior of said housing. This tube opens into said interior through a plurality of holes 46 in its side close to the far end which receive the cleansed fluid for subsequent discharge. The top end of tube 44 is covered with a flat topped cylindrical shroud 48 which is adapted to contain and channel said cleansed fluid into holes 46. Also contained in bottom 36 is a machined channel 50 which acts to channel the separated solid particles into hole 32 and chamber 28 for collection by magnet 34. Channel 50 is machined into the bottom 36 so that its sides are tangent to the flow of fluid. It has been experimentally found that the channel 50 substantially increases effectiveness of particle reception by hole 32.

In use the system takes advantage of the differences in mass between gas, fluid, and solid particles. When a fluid mixture of different massed components is subjected to a rotational flow it creates a centrifugal force field. In such a field the outward centrifugal velocity achieved, all other factors being equal, of the particle being accelerated varies directly with the mass. Thus in such a field the relatively heavy solid particles will move fastest and farthest away from the center of rotation while the very light gas bubbles in the foam will be the slowest and move outward the least. The construction of the invention is designed to create such a force field and take advantage of those differences. In the preferred embodiment, as noted above, the fluid being cleaned is injected tangentially through inlet 16 into the interior of chamber 12. Inlet 16 is designed to cooperate with top 14 and hollow tubes 24 and 44 to create a downwardly directed cyclonic spiral flow pattern in the annulus which lies between smooth inner wall 18 and said hollow tubes. This cyclonic flow creates the centrifugal force field needed to quickly force the heavy solid particles to the outer reaches of said flow pattern while, at the same time allowing the gas bubbles to coalesce in the center of the pattern. As shown in FIG. 2 the flat top surface 54 of shroud 48 extends far enough out into the interior of housing 12 so that said coalesced bubbles cannot travel very far down the length of said housing with the spiraling fluid. This forces them into opening 25 of tube 24 for ultimate discharge out of the system through channel 22 and gas outlet 20. Under some circumstances to maintain system pressure, outlet 20 leads to a pressure valve (not shown) which only opens when the gas pressure exceeds a predetermined amount. Quantities of oil which may be inadvertantly swept out with the collected foam and gases can be returned to the main oil sump where standard atmospheric breather vents would displace the gas and the oil would be recovered for subsequent reuse.

The spirally rotating fluid will not be affected by the shroud extension and will continue in its downward pattern along with the metal chips. When the flow pattern reaches bottom plate 36 it reverses itself and flows in a generally upward path along tube 44 into shroud 48. This, as noted, channels the flow through holes 46 into hollow tube 44, fluid discharge 42 and back into the system (not shown). As the flow pattern reverses itself it creates a second centrifugal force field which propels the separated particles down to the bottom 36 of housing 12 and keeps them there. The rotation of the cyclonic flow pattern tends to drag the particles around bottom plate 36 until they fall into machined channel 50 which directs them through hole 32 for collection by magnet 34.

In developing the present invention it was found that the effectiveness and operability thereof, both with respect to particles and air separation, was very dependent upon the dimensions of the various components. Referring now to FIG. 2 the bottom portion of the interior diameter of housing 10 is increased by taper 59 of the interior wall 18. The angle of taper 59 with respect to the vertical interior wall 18 is shown as $\theta$. Tests have shown that with no taper, or $\theta = 0°$, particle capture efficiency E was substantially less than when $\theta = 15°$. For instance, for 200 micron size particles, particle capture efficiency E equalled 36% for $\theta = 0°$ and increased to 58% when $\theta$ was increased to 15°. For 500 micron size particles captured efficiency E increased to 84% from 69% for $\theta = 15°$ as compared to $\theta = 0°$. For optimum capture efficiency $\theta$ should be within the range of 10° to 20°. Changes in $\theta$ did not affect the efficiency of air separation from the system.

The tangentially machined groove 50 also affects particle capture efficiency. It has been found that for 500 micron size particles capture efficiency E increased by 12% as compared with the efficiency of the system with no slot present. Particle capture efficiency E increased by 20% with respect to 1,000 micron size particles with the addition of the slot.

Various other dimensions of the system are shown in FIG. 2. The distance between air exit orifice 25 and the top of shroud 54 is x while the vertical length of the shroud is z. The distance of the bottom of the shroud from the interior bottom 36 of the housing 10 is y, while the overall vertical length of the interior of the housing 10 is t. The interior diameter of the housing 10 is v, while the exterior diameter of the shroud 48 is w. The distance of orifice 25 from the top of the interior chamber of housing 10 is shown as s. In testing various configurations of the invention during its development phase, the interior diameter v of housing 10 was treated as a constant. In the preferred embodiment of the invention v was 2 inches. Of course, the actual dimension of v is a function of the flow and mass rates of the system in which the invention is to be used. Various configurations were tested varying some of these dimensions.

In general, it has been found that the following relationships between the various aforesaid dimensions provide an extremely efficient system: $s = v/4$, $x = s/2$ which equals $v/8$, $t = 1.37 v$, $w = 0.56 v$, $z = 0.35 v$, $y = 0.66 t$, and $r = v/16$.

During testing, for example, it was found that shroud diameter $w = 0.56 v$ was close to an optimum insofar as efficiency in removing air from the system. Such efficiency was measured by monitoring the amount of oil which was transmitted through orifice 25 along with the air being removed from the system. In the preferred embodiment for $v = 2$ inches, $w = 1.12$ inches and resulted in 12 ounces of oil per minute being passed through orifice 25. With shroud diameter w increased to 1.37, the oil loss increased to 16 ounces, and when the diameter was decreased to 0.75 inches the amount of oil lost dramatically increased to 27 ounces.

Through qualitative visual flow techniques it was found that the interior diameter of orifice 25 worked efficiently with a diameter of 0.14 inches while the amount of oil lost through orifice 25 increased subtantially when the diameter of orifice 25 was increased to 0.31 inches.

Testing has shown that highly effective performance, with respect to particle removal efficiency E, is obtained when $t = 1.37 v$ or 2.75 inches in the preferred embodiment. It was found the $E = 58\%$, 98% and 100%, respectively, for 200 micron, 500 micron and 1,000 micron size particles. Tests with $t = 1.75$ showed particle removal efficiency E was 58%, 72% and 92%, respectively, for 200 micron, 500 micron and 1,000 micron size particles.

As previously suggested, the design of the preferred embodiment is such that essentially all particles having a mass of $2.26 \times 10^{-5}$ g (equal to a steel sphere with a diameter of 200 microns) or greater will be effectively removed from the fluid being treated. Smaller "fuzz" particles are not as greatly affected by the two centrifugal force fields and most of these relatively innoccuous particles are swept out of the treatment system thus allowing for an effective means of sorting and segregating failure particles from general noncritical mass of particulate material in the fluid. Detector 24 can be of any conventional design. In the preferred embodiment it is of the type which has a gap 56 which when bridged by one or more particles will send out an electrical signal through connector 58, thus warning the operator of a possibly critical problem developing somewhere in the system. Such a warning will permit effective maintenance and repair before a catastrophic failure will develop.

Although the present invention has been described with reference to the particular embodiment herein set forth, it is understood that the present disclosure has been made only by way of example and that numerous changes in the details of construction may be resorted to without departing from the spirit and scope of the invention. Thus the invention should not be limited by the foregoing specification but rather only by the scope of the claims appended hereto.

What is claimed is:

1. In the pressurized lubrication system for mechanical drives, a particle separator adapted to remove entrapped gases and to separate failure particles from wear particles and segregate them for subsequent removal comprising:

a cylindrical housing having a smooth inner wall;
   a fluid inlet adapted to tangentially inject the fluid into said housing;
   a gas removing means having an outlet in the top of said housing;
   a first hollow cylindrical tube within said housing and concentric with it depending downward from said gas outlet and adapted to cooperate with said fluid inlet such that when the fluid is injected into the annulus between said first tube and said inner wall, a downwardly directed spiral flow pattern is developed, said flow pattern generating a centrifugal force field which firstly causes the entrapped gases to coalesce substantially in the center of said flow pattern and secondly selectively propels failure particles to the outer reaches of said pattern for eventual separation, capture and removal;
   fluid removal means having an outlet in the bottom of said housing;
   a second hollow cylindrical tube within said housing and concentric with it depending upward from said fluid outlet and adapted first to cooperate with said first tube to maintain said downward spiral flow pattern and said centrifugal force field and then to cooperate with said bottom to create a second centrifugal force field which causes said failure particles to be selectively propelled to and kept at the bottom of said housing from which location they are cpatured for removal;

means adapted for receiving said separated failure particles connected to said housing whereby they are segregated and trapped for subsequent removal from the system; and means for detecting and indicating the presence of failure particles, connected to said receiving means.

2. The apparatus of claim 1 wherein said gas removing means comprises:

said hollow first tube, having a first opening at the far end thereof to receive said coalesced gases;

an internal channel connecting said tube to said gas outlet; and said second hollow tube, further comprising a flat topped cylindrical shroud at the end thereof, said shroud being adapted to intercept said coalesced gases and prevent them from travelling further downward toward the bottom of said housing and then direct them into said first opening in said first hollow tube for discharge from the system.

3. The apparatus of claim 1 wherein said fluid removal means comprises said second hollow tube adapted to cooperate with the bottom of said housing to reverse the spiral flow pattern and force the fluid to flow back alongside said hollow tube upwardly into said shroud, said shroud being adapted to contain and direct said flowing fluid into a plurality of second openings in the side of said hollow tube whereby said fluid is admitted to said fluid outlet for discharge from the system.

4. The apparatus of claim 2 or 3 wherein said receiving means comprises a channel in the bottom of said housing adapted to receive said failure particles after they have been propelled out of said flow pattern by said second force field and further adapted to conduct said particles through a hole in the side of said housing into a chamber alongside said housing which acts to segregate and trap said failure particles, said chamber further containing said detecting means which includes a magnetic particle detector positioned with the magnet thereof across said hole from said channel and adapted to signal the presence of trapped failure particles.

* * * * *

UNITED STATES PATENT AND TRADEMARK OFFICE
CERTIFICATE OF CORRECTION

PATENT NO. : 4,282,016
DATED : August 4, 1981
INVENTOR(S) : Thomas E. Tauber and George E. Chapman It is certified that error appears in the above-identified patent and that said Letters Patent are hereby corrected as shown below:

In claim 1:
Column 7, line 4, delete the word [cpatured] and insert in its stead the word captured.

Signed and Sealed this

Twentieth Day of October 1981

[SEAL]

Attest:

Attesting Officer

GERALD J. MOSSINGHOFF

Commissioner of Patents and Trademarks